(12) United States Patent
Zadro

(10) Patent No.: US 7,888,657 B1
(45) Date of Patent: Feb. 15, 2011

(54) ULTRAVIOLET WATER AND OBJECT SURFACE DISINFECTION APPARATUS

(76) Inventor: Zlatko Zadro, 5422 Argosy Dr., Huntington Beach, CA (US) 92649

( * ) Notice: Subject to any disclaimer, the term of this patent is extended or adjusted under 35 U.S.C. 154(b) by 346 days.

(21) Appl. No.: 12/290,698

(22) Filed: Nov. 3, 2008

(51) Int. Cl.
*A61L 2/10* (2006.01)

(52) U.S. Cl. ............................. 250/455.11; 250/504 H; 422/186.3

(58) Field of Classification Search ............ 250/455.11, 250/453.11, 454.11, 504 H, 504 R; 422/22, 422/24, 186.3
See application file for complete search history.

(56) References Cited

U.S. PATENT DOCUMENTS

2008/0260601 A1* 10/2008 Lyon ........................ 422/186.3

* cited by examiner

*Primary Examiner*—Kiet T Nguyen

(74) *Attorney, Agent, or Firm*—William L. Chapin

(57) ABSTRACT

An apparatus for alternatively disinfecting an object surface and a liquid comprising a hollow handle base graspable in a human hand, an electrical power source contained within a hollow interior space of the handle base housing for supplying electrical power to an ultraviolet lamp, a lid including a lamp support bulkhead, and an ultraviolet lamp mounted to the lamp support bulkhead. A tubular cover shell is releasably attachable to the lamp support bulkhead. The cover shell has an upper wall which is opaque to ultraviolet radiation and a lower wall which has therein an aperture which is transmissive to ultraviolet radiation. A hinge joint pivotably joins the lamp support bulkhead of the lid to the handle base housing, the hinge joint enabling the lid to be pivoted from a first, compact storage and transport orientation in which the lower wall of the lid cover shell overlies the handle base housing, and the upper wall of the lid cover shell overlies the ultraviolet lamp to a second, use orientation in which the lid is positionable above an object surface to thereby locate the aperture adjacent to the object surface. The cover is alternatively releasably removable to expose the ultraviolet lamp and enable it to be immersed in a liquid to disinfect the liquid. Sensor probes protrude from the bulkhead near the ultraviolet lamp prevent operation of the lamp unless the probes are in contact with a liquid.

31 Claims, 14 Drawing Sheets

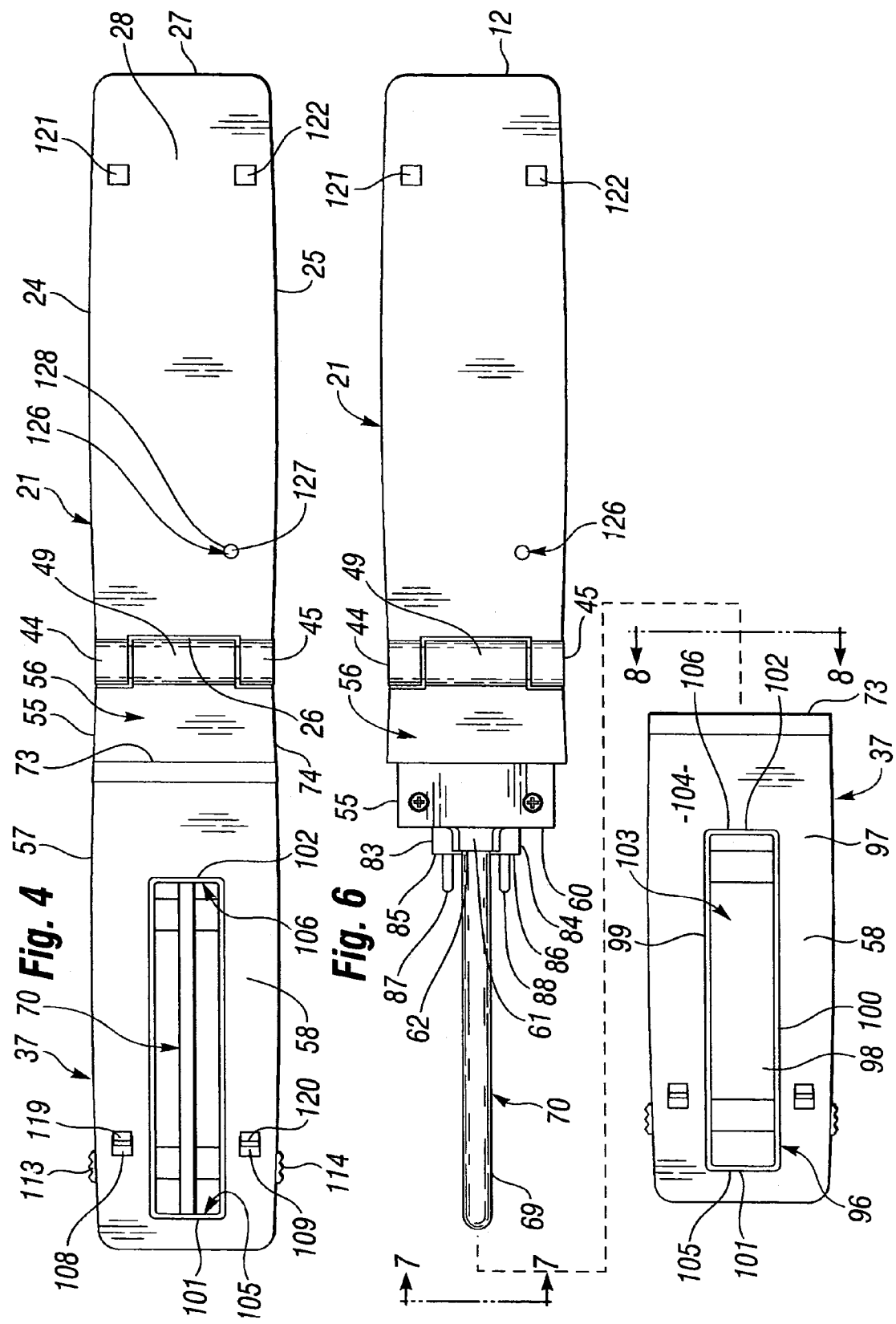

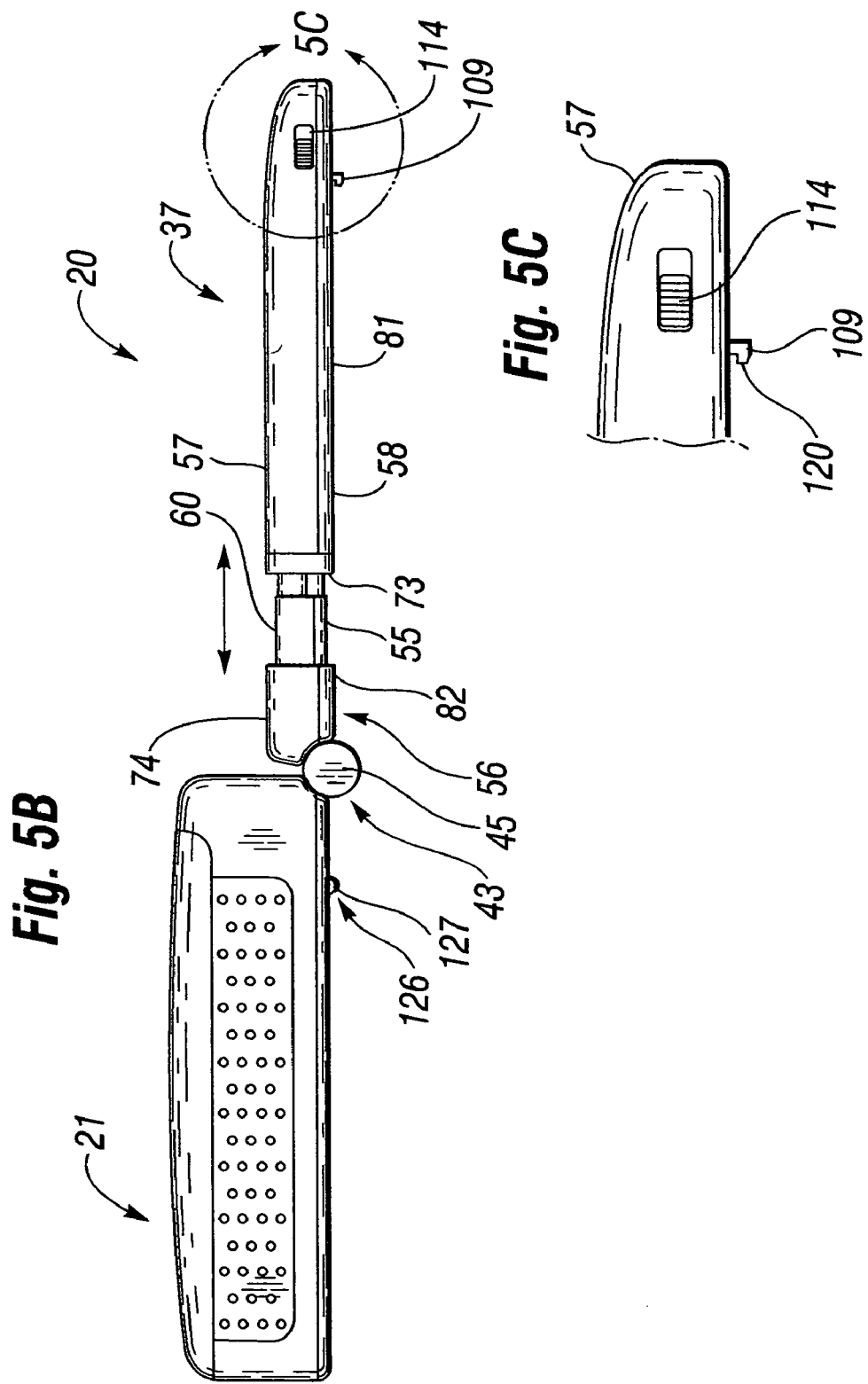

ULTRAVIOLET WATER AND OBJECT SURFACE DISINFECTION APPARATUS

BACKGROUND OF THE INVENTION

A. Field of the Invention

The present invention relates to portable devices for disinfecting surfaces of objects, or drinking water, of potentially harmful organisms. More particularly, the invention relates to a dual function ultraviolet water and object surface disinfection apparatus which is effective in killing harmful organisms on surfaces such as telephone handsets, and in drinking water contained in a cup, glass or other small drinking vessel.

B. Description of Background Art

According to the U.S. Environmental Protection Agency, indoor air can be up to 70 times more polluted than the outside atmosphere. Moreover, it is reported that 90% of colds and flu germs are spread in enclosed environments, such as school rooms, office buildings, airplane cabins and the like. For example, virus-causing micro-organisms can be responsible for as many as ten colds per year for the school-age child. Some cold and flue viruses can survive on surfaces such as handrails, door knobs, telephone handsets, for up to 72 hours—giving plenty of time for classmates, family members or fellow travelers to be infected. Accordingly, it would be desirable to provide an efficient means for disinfecting surfaces which people may touch or contact. One such means consists of spraying a potentially infected surface with a germicidal spray, or wiping the surface with a cloth or paper towel moistened with a germicidal substance such as isopropyl alcohol. Thus, some grocery stores are now providing a cannister of alcohol-saturated towels or "wipes" at store entrances which shoppers may use to wipe down the handles of shopping carts. Although the use of germicidal wipes is an effective means for disinfecting surfaces, that method is impractical or impermissible in many situations.

Harmful microorganisms in the food preparation areas of restaurants or home kitchens also pose potential health risks. For example, food cutting boards are a prime source of potential transmission of harmful microorganisms to humans. When unwashed meat or salmonella can infect the board. The organisms can than be transmitted to other food items which are subsequently cut on the board. Although cutting boards could be disinfected with a germicidal agent such as alcohol applied from an aerosol spray can or an alcohol-moistened wipe, this technique would generally be impractical because residual traces of the germicidal substance, if not harmful to humans, could impact undesirable bad tastes to foods prepared on a cutting board after treatment. Accordingly, a need still exists for a disinfection apparatus which may be used on cutting boards and other articles used in the preparation of foods.

Another health problem which is frequently encountered by travelers to other countries, particularly underdeveloped and/or mis-managed countries, is contaminated drinking water. This problem is also encountered by hikers, hunters, campers and other outdoor persons. Thus, water sources such as streams and ponds, even those remote from human habitation and ensuing likelihood of human contamination, are frequently infected with harmful bacteria or other microorganisms. These include parasites such as Ghardaia, a paramecium found in the fecal matter of domestic as well as wild cattle. Accordingly, it would be desirable to provide a portable waster disinfection unit which could be used by an outdoorsman or traveler to disinfect a small quantity of water contained in a drinking cup or glass, prior to drinking the water.

In apparent recognition of the need for a portable water disinfection device, Maiden et al., U.S. Pat. Nos. 5,900,212 and 6,110,424 disclosed a hand-held water purification system which includes a pen-light sized ultraviolet lamp that is enclosed in a water impervious quartz cover and powered by a battery and associated ballast circuitry. The battery and ballast circuitry are connected to the lamp by switches that are under the control of a liquid level sensor. The sensor connects the battery, the ballast circuitry and the lamp once the sensor determines that the ultraviolet lamp is fully immersed in the water, thus irradiating the water with short-wave ultraviolet radiation in the germicidal range, i.e., around 254 nanometers (nm), to kill organisms in the water.

Maiden, U.S. Pat. No. 6,579,495 disclosed a hand-held ultraviolet water purification system using solid-state light emitting diodes rather than the mercury vapor lamp disclosed in the aforementioned Maiden et al. patents.

The foregoing devices may be assumed to be effective in killing harmful organisms contained in drinking water and contained in a small vessel such as a water glass or cup. However, there remained a need for a portable surface disinfection unit. In response to that need, the present applicant began marketing in 2006 a surface disinfection device under the name Nano-UV Disinfection Light Scanner. That device has generally the form-factor of a small portable hand-held cellular phone. When the lid of the device is flipped up into longitudinal alignment with the base of the device, an aperture in the lid is exposed. An ultraviolet lamp within the lid and aligned with the aperture is energized by an electronic ballast circuit and batteries contained within the device, when a switch on the device is operated. With the ultraviolet lamp and aperture facing downwards, the device is held and moved in a scanning motion over the surface of an object such as a telephone handset or the like, to thus kill the germs and other harmful microorganisms on the surfaces of the object. The present invention was conceived of to provide a dual function water and object surface disinfection apparatus which provide a highly effective means for killing bacteria and other harmful microorganisms, both on the surfaces of objects and within water contained in a drinking vessel.

OBJECTS OF THE INVENTION

An object of the present invention is to provide an apparatus for killing microorganisms harmful to humans which are present on object surfaces or in water which is to be drunk.

Another object of the invention is to provide a portable dual function water/object surface disinfection apparatus which uses ultraviolet radiation to kill microorganisms in contaminated water contained in a small drinking vessel to thereby render the water safe for human consumption, and alternatively to kill microorganisms on surfaces of objects to be contacted by a person, such as a telephone handset.

Another object of the invention is to provide a hand-held portable dual function water/object surface disinfection apparatus which utilizes a low-pressure mercury vapor discharge lamp which has a tubular body that is unjacketed to thereby enable ultraviolet radiation emitted over a wide spectral bandwidth by the lamp discharge to be transmitted directly to water or onto an object surface and thereby efficiently kill microorganisms present in the water or on the object surface.

Another object of the invention is to provide a dual function portable water/object surface disinfection apparatus which includes a handle base housing that contains batteries and electronic ballast circuitry, and a lid pivotable from a closed, inoperative position conformally overlying and latched to the base, enabling the apparatus to be conveniently stowed in a pocket or purse, to an operating position in which the lid is longitudinally aligned with the handle base to thus expose an ultraviolet lamp within the lid, the handle base and the apparatus being rotatable around a common longitudinal axis to position the lamp above and irradiate an object surface.

Another object of the invention is to provide a dual function portable water/object surface disinfection apparatus which includes a handle base, a "flip-top" lid pivotably attached to the handle base, the lid including a longitudinally elongated tubular ultraviolet lamp protruding from a lamp support bulkhead, and a tubular cover shell including a reflector cover and base plate which is slidably removable from the bulkhead from a first configuration in which a reflector adjacent to the upper inner surface of the cover lid is effective in reflecting ultraviolet light emitted by the lamp tube downwards through a rectangular aperture through the base plate and onto a surface of an object to be disinfected, the apparatus having a second configuration in which the cover shell is slidably removable from the bulkhead to fully expose the lamp for immersion into water in a drinking vessel to thereby disinfect the water.

Another object of the invention is to provide a portable, pocket-carryable dual function water/object surface germicidal disinfection apparatus which includes a hollow handle base containing batteries and a lamp power supply ballast, a flip-top lid having a rear hinge block pivotably attached to the handle base, the lid having an ultraviolet lamp tube which protrudes from a lamp support bulkhead on the front of the hinge block, and a tubular cover shell including an upper cover wall protruding upwards from a base plate, the cover shell being slidably removable from the lamp support bulkhead to fully expose the ultraviolet lamp, and a pair of sensor probes protruding from the bulkhead which are interconnected with control circuitry that enables the power supply to energize the lamp when the protruding lamp tube is inserted into water in a container sufficiently far for the sensor probes to contact the water.

Various other objects and advantages of the present invention, and its most novel features, will become apparent to those skilled in the art by perusing the accompanying specification, drawings, claims, and abstract.

It is to be understood that although the invention disclosed herein is fully capable of achieving the objects and providing the advantages described, the characteristics of the invention described herein are merely illustrative of the preferred embodiments. Accordingly, I do not intend that the scope, of my exclusive rights and privileges in the invention be limited to details of the embodiments described. I do intend that equivalents, adaptations and modifications of the invention reasonably inferable from the description contained herein be included within the scope of the invention as defined by the appended claims.

SUMMARY OF THE INVENTION

Briefly states, the present invention comprehends a portable, hand-held, pocket carryable, self-contained, battery-powered apparatus which emits ultraviolet light effective in disinfecting object surfaces as well as water contained within a small vessel.

An ultraviolet water and object surface disinfection apparatus according to the present invention includes a longitudinally elongated, hollow rectangular box-shaped base housing which serves as a handle. The apparatus has a lid which has a similar outline shape to that of the handle base. The lid is pivotably attached to the base in a conformally overlying, closed inoperative position by a cylindrical hinge-joint disposed transversely along short vertically aligned edges of the handle base housing and lid.

The disinfection apparatus according to the present invention includes a low-pressure mercury vapor discharge lamp contained within the lid. The lamp has an elongated straight, slender cylindrically-shaped body which contains therein a hermetically sealed hair-pin curve shaped capillary bore having parallel side-by-side legs. A rear base end of the lamp, opposite the front outer end where the hair-pin curve is located, has protruding rearwardly therefrom a pair of electrical lamp connector pins which penetrate sealed end walls of the capillary bore legs. The lamp emits ultraviolet radiation when high voltage current is supplied to the lamp electrodes. The high-voltage current is provided by a power supply which is located in the handle base housing, and supplied with low-voltage current from batteries contained in a battery compartment located within the housing. The power supply for powering the ultraviolet lamp by batteries is a DC-AC inverter which includes a transistor oscillator and step-up transformer. Such power supplies are well known in the art and commonly referred to as "electronic ballasts."

The disinfection apparatus according to the present invention includes a lamp support bulkhead which forms part of the lid and protrudes outwardly away from a hinge block which comprises part of the hinge joint that joins the lid to the handle base housing. With this construction, when the lid is pivoted away from the handle base into longitudinal alignment with the handle base, the lamp support bulkhead and lamp tube protrude outwardly from the hinge joint, in parallel alignment with the longitudinal axis of the handle base.

According to the present invention, the lid includes a tubular cover shell which encloses the ultraviolet lamp. The lid cover shell has an arcuately curved, convex upper wall that comprises the upper surface of the apparatus when the lid is pivoted downwards into contact with handle base housing to thus place the apparatus in a closed, inoperative carrying and storage configuration. The lid cover shell also has a lower flat base plate which overlies the upper surface of the handle base housing in the closed configuration of the apparatus.

The base plate of the lid cover shell has through its thickness dimension a longitudinally elongated, rectangularly-shaped exit aperture which is generally concentric with the outline shape of the base part. The aperture is vertically aligned with the ultraviolet lamp tube, which as stated above, has the shape of a long, thin transparent cylinder that contains therewithin a tubular hair-pin shaped, twin-legged capillary bore. The base plate aperture provides an un-obstructed path for ultraviolet radiation emitted from the ultraviolet lamp to the surface of an object over which the lid is positioned in an inverted, face-down orientation.

A preferred embodiment of the disinfection apparatus includes a reflector box contained within the cover shell, which has an outline shape similar to that of the aperture through the base plate of the lid. The reflector box has an upper reflective wall and reflective side walls which enclose the ultraviolet lamp tube, and an open bottom adjacent to the lid aperture. The upper wall of the reflector box, which preferably has a concave inner surface located, above the ultraviolet lamp tube and the side walls, redirect ultraviolet radiation emitted upwardly and laterally from the tube to a downward direction and thence through the base plate aperture, thus increasing the radiation intensity on an object surface.

As thus far described, the apparatus according to the present invention provides a highly efficient means for disinfecting object surfaces. Disinfection is accomplished by opening the lid into longitudinal alignment with the handle base housing, turning the apparatus over so that the lid base plate aperture faces downwardly towards the surface of an object to be disinfected, operating an electrical switch on the handle base housing to provide electrical power to the ultraviolet lamp, grasping the handle base housing in the hand, and moving the apparatus in a sweeping, overlapping scanning motion a short distance above an object surface to be disinfected. Importantly, however, the disinfection apparatus according to the present invention includes novel structural and functional characteristics in addition to those described above, which enable the apparatus to be used alternatively to disinfect drinking water contained in a small container such as a drinking glass or cup. Those additional structural and functional characteristics will now be described.

According to the invention, the lid cover shell described above includes a relatively long, thin upper arched wall which protrudes upwardly from a thin, longitudinally elongated, rectangular base plate. The upper wall of the lid cover shell has a generally uniform, inverted U-shaped transverse cross sectional shape. Thus, the lid cover shell has the shape of an elongated tubular body which has disposed longitudinally through its length a semi-oval shaped bore, which penetrates the rear transverse end wall of the body. The cover shell is closed at a front end thereof by a convex, arcuately curved, front transverse end wall which is disposed between the upper wall and base plate.

The lid includes a short hinge block located above the upper surface of the base plate, near the rear transverse edge of the base plate, and a lamp support bulkhead which protrudes forward from the hinge block. The bulkhead structure protrudes outwardly from the hinge block, which joins the lid to the handle base housing.

The lid hinge block has in lower plan view the shape of a rectangular T-shaped block which has a rear reduced width end portion that forms a transversely disposed hinge cylinder. The hinge cylinder fits between and in coaxial alignment with a pair of laterally spaced apart shorter cylindrical hinge support bosses which protrude forward from a front transverse edge wall of the handle base housing. A hinge pin disposed laterally through coaxially bores through the two hinge support bosses of the handle base housing, and the centrally located lid hinge cylinder, facilitates pivotable movement of the lid from a closed position overlying the base housing, to an outwardly pivoted use position in longitudinal alignment with the base housing.

According to the invention, the lid hinge block has protruding from a front transversely disposed, vertical end wall thereof a laterally centrally located, reduced width lamp tube support bulkhead. The bulkhead has in plan view a transversely elongated rectangular shape. In front elevation view, the bulkhead has a flat base which is recessed upwardly to receive a rear transverse edge wall of the base plate, which abuts a vertically disposed shoulder of the bulkhead. The upper surface of the bulkhead has a convex, arcuately curved surface. Thus, the lamp tube support bulkhead has a uniform, semi-oval transverse cross-sectional shape that is adapted to be inserted into and conformally received within the rear entrance opening to the bore longitudinally disposed through the lid cover shell.

A front, outer transversely disposed front vertical end wall of the bulkhead has protruding perpendicularly forwardly therefrom a generally cylindrically-shaped lamp tube support boss. A pair of laterally spaced apart lamp pin sockets extend into the front face of the lamp support boss. The lamp pin sockets, which are made of a conductive metal such as copper, receive in an interference fit a pair of laterally opposed cylindrical lamp terminal pins which protrude rearwardly from the base of the ultraviolet lamp, which has the shape of a narrow, hairpin-shaped U-tube. A pair of flexible wires disposed through the hinge joint connect the lamp pin sockets to output terminals of the high-voltage power supply within the base housing.

According to the invention, the lid cover shell is releasably connected to the bulkhead by a fastener assembly that enables the cover shell and base plate to be grasped and pulled longitudinally forward from the lamp support bulkhead to thus fully expose the ultraviolet lamp tube, which may then be inserted into water contained in a vessel to thereby irradiate and disinfect the water.

In a preferred embodiment, the releasable fastener assembly which joins the bulkhead to the cover shell and base plate of the lid includes a pair of cylindrical fastener pins which protrude forward from the bulkhead. The releasable fastener assembly includes an elastically deformable member fixed to the base plate and cover shell of the lid, which resiliently receives the fastener pins. The fastener pins have a cylindrical shape and arcuately curved, convex outer transverse ends.

Preferably, there are two fastener pins, one each protruding perpendicularly forwards from the front transverse end wall of an individual one of a pair of cylindrical fastener pin bosses located on opposite sides of the lamp tube support boss. The fastener pins are laterally aligned, and receivable in an interference fit within an inverted C-shaped metal spring strip which protrudes upwardly from the base plate of the lid. With this construction, the lid cover shell remains securely fastened to the lamp support bulkhead by spring tension exerted by the spring strap against the outer sides of the two fastener pins and by a conformal interference fit between the outer longitudinally disposed peripheral surface of the lamp support bulkhead and the inner longitudinally disposed surface of the lid cover shell bore. This construction also enables the lid cover shell to be longitudinally slidably removed from and reattached to the bulkhead.

According to the invention, the apparatus includes electronic sensor control circuitry which is connected to the power supply. With the lid cover shell removed from the lamp support bulkhead, the sensor circuitry prevents the ultraviolet lamp from being energized unless the lamp is fully immersed in water. A pair of water sensor probes which are electrically connected to the sensor control circuitry disables the power supply unless both probes are immersed in water.

In a preferred embodiment, electrical connections are made by flexible wires between the sensor control circuitry, which is located in the handle base housing, and the two fastener pins. This novel construction enables the fastener pins to function as liquid sensing probes, in addition to performing fastening functions. Moreover, using a conductive metal fastener spring strap in the lid cover establishes electrical continuity between the fastener pins, thus enabling the power supply to function when the lid cover shell and base plate are re-fastened to the bulkhead after the apparatus has been used to disinfect water.

The dual function apparatus according to the present invention is used to disinfect water by slidably removing the lid cover shell from the lid bulkhead, immersing the bare, unjacketed ultraviolet lamp bulb into water contained in a small vessel such as a drinking glass or cup, grasping and moving the handle base to thus move the protruding lamp bulb in a stirring motion through the water, for a period of about 10 seconds.

BRIEF DESCRIPTION OF THE DRAWINGS

FIG. 4 is a lower plan view of the apparatus of FIG. 1, showing a lid thereof pivoted upwards from a handle base thereof in an inoperative, closed configuration to an operative configuration in longitudinal alignment with the handle base.

FIG. 5B is a side perspective view of the structure of FIG. 5A, showing the lid cover shell more fully disengaged from the hinge block.

FIG. 5C is a fragmentary view of the apparatus of FIG. 5A, on an enlarged scale.

FIG. 6 is a lower plan view similar to that of FIG. 5A showing the lid cover shell fully removed.

DESCRIPTION OF THE PREFERRED EMBODIMENTS

FIGS. 1-16 illustrate various aspects of an ultraviolet water and object surface disinfection apparatus according to the present invention.

Figure 1:
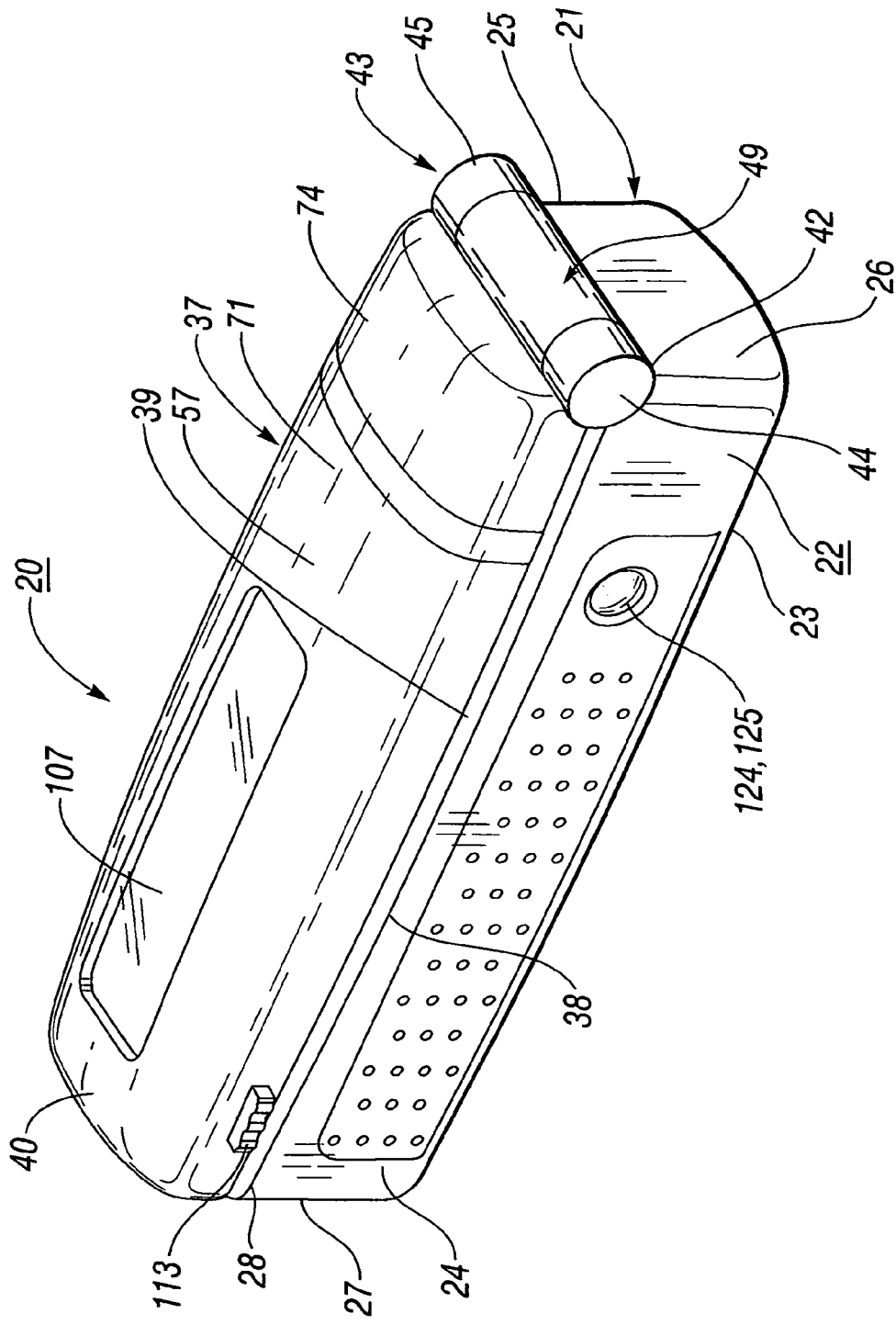
FIG. 1 is a lower, left-side perspective view of an ultraviolet disinfection apparatus for object surfaces and drinking water according to the present invention.
Figure 3:
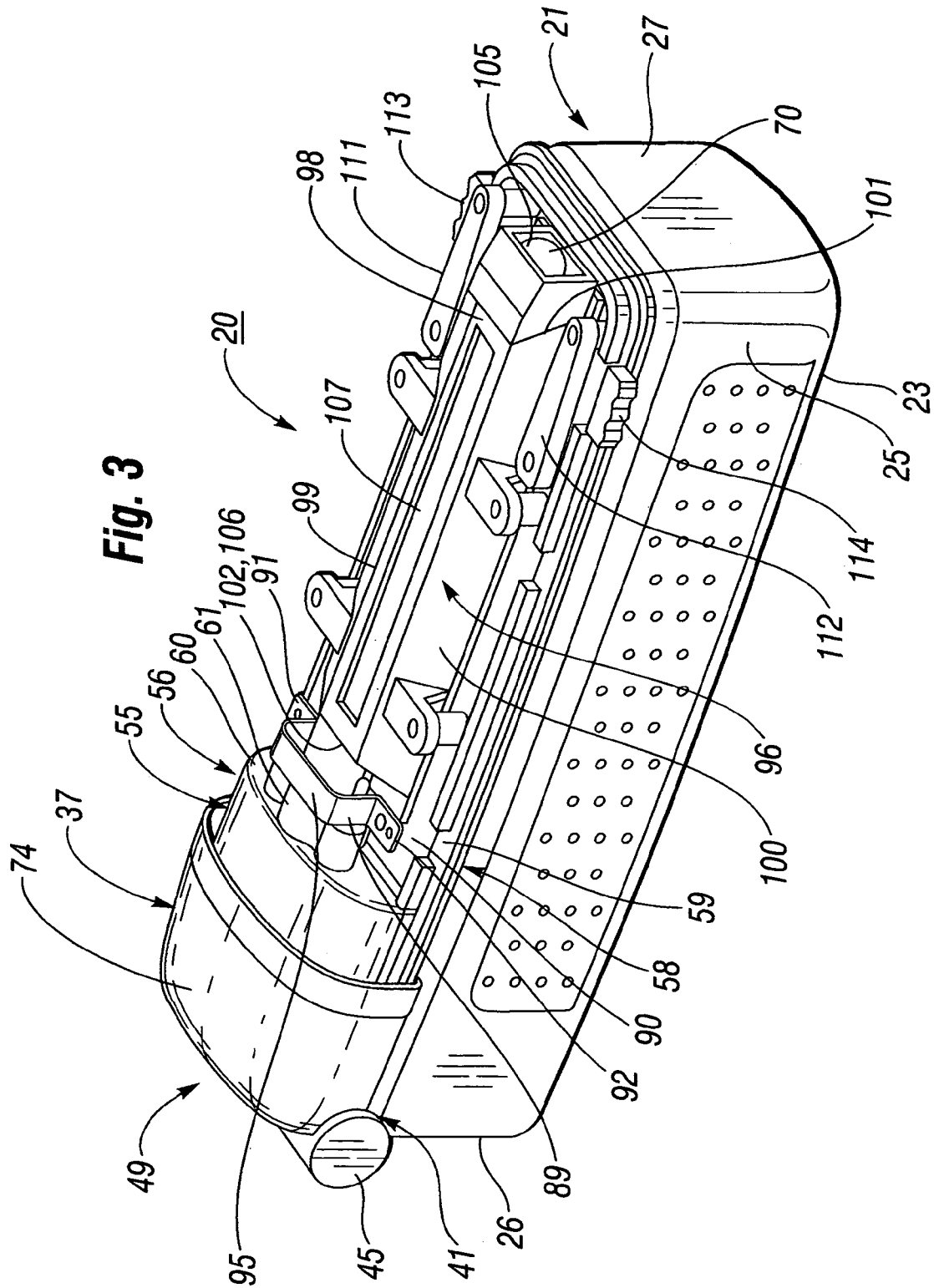
FIG. 3 is a partly broken-away lower, right-side perspective view of the apparatus of FIG. 1.
Figure 5A:
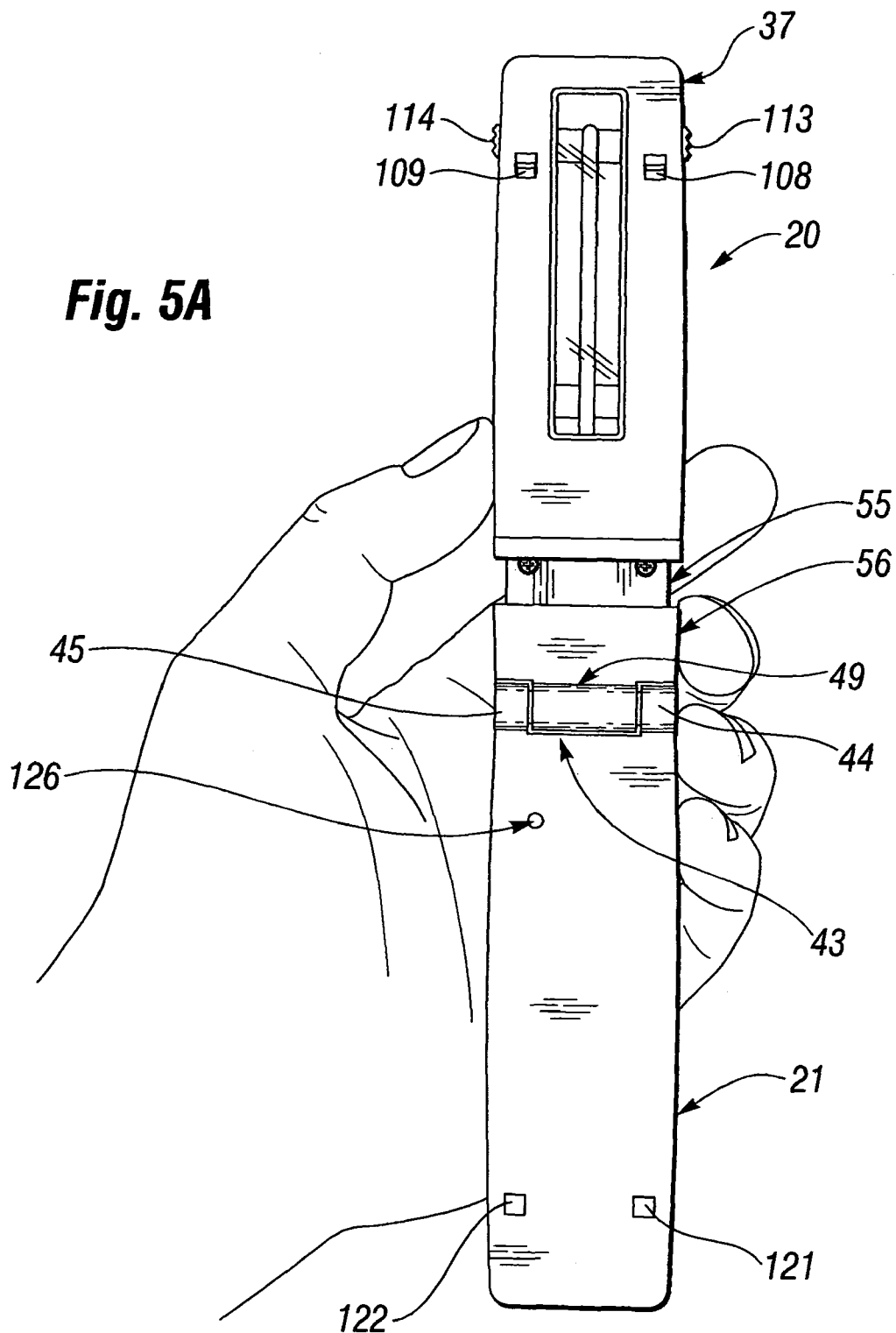
FIG. 5A is a lower perspective view of the apparatus of FIG. 1, showing a cover shell of the lid partially slidably disengaged from a lamp support bulkhead of the lid.
Figure 7:
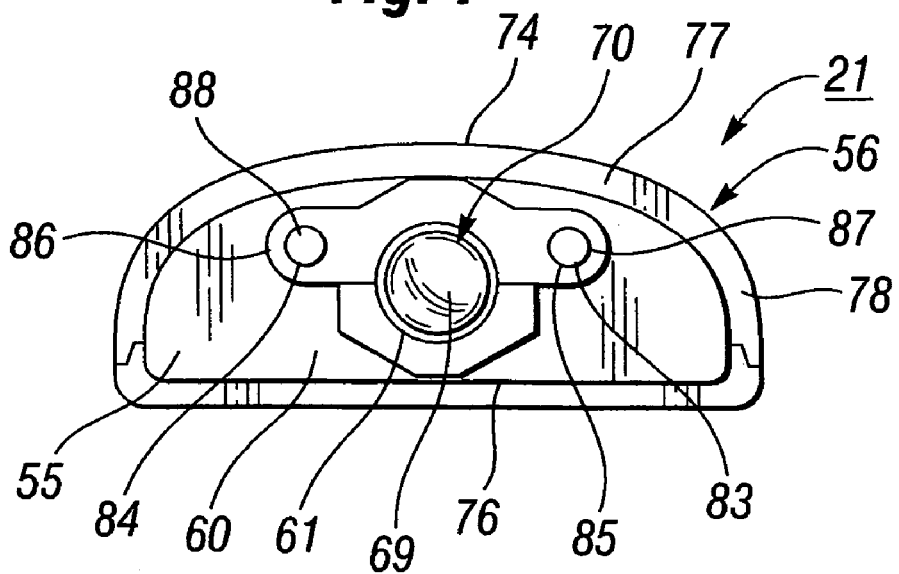
FIG. 7 is a front elevation view of a handle base housing portion of the apparatus of FIG. 6, taken in the direction of line 7-7.

FIGS. 1 and 3 are lower perspective views showing an inverted ultraviolet water and object surface disinfection apparatus 20 according to the present invention. As shown in FIGS. 1 and 3, apparatus 20 includes a handle base housing 21 which has the shape of a longitudinally elongated rectangular box 22 having a flat rectangular upper base wall 23. Upper base wall 23 has longitudinally elongated, rectangularly-shaped left and right flange walls 24, 25 which protrude downwardly from left and right edges of the base wall, and shorter front and rear transverse edge flange walls 26, 27 which protrude downwardly from front and rear edges of the base wall. The lower edges of the four downwardly depending flange walls 24, 25, 26, 27 of base housing 21 are coplanar, and terminate in a lower cover wall 28 which has a shape similar to, and is vertically aligned with, base wall 23, as shown in FIG. 3.

Figure 9:
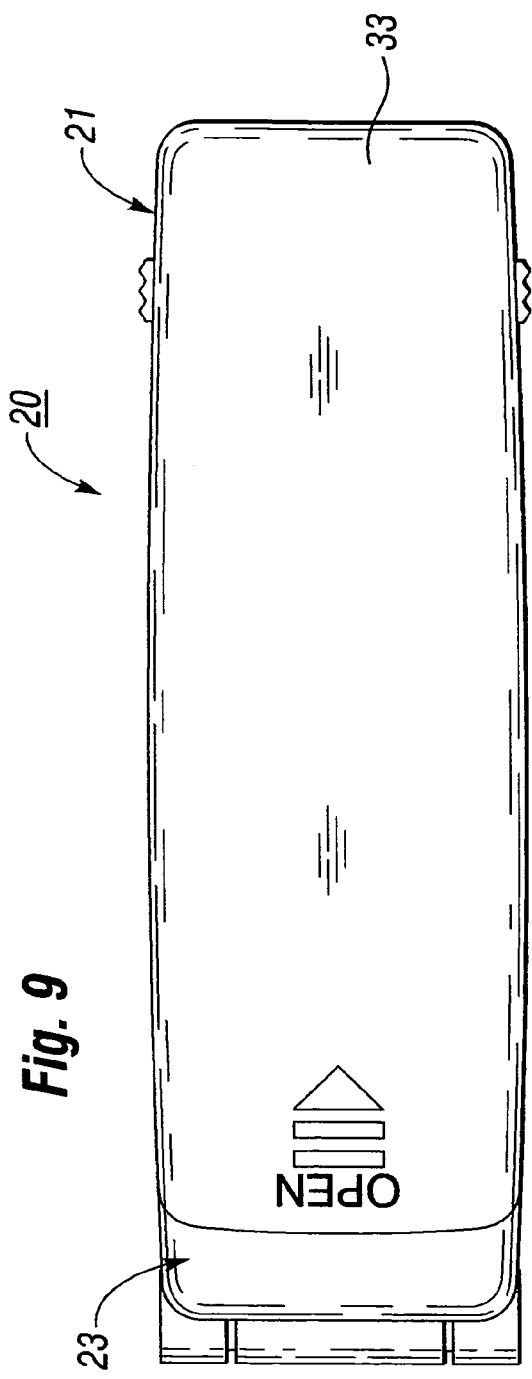
FIG. 9 is an upper plan view of the apparatus of FIG. 1.
Figure 10:
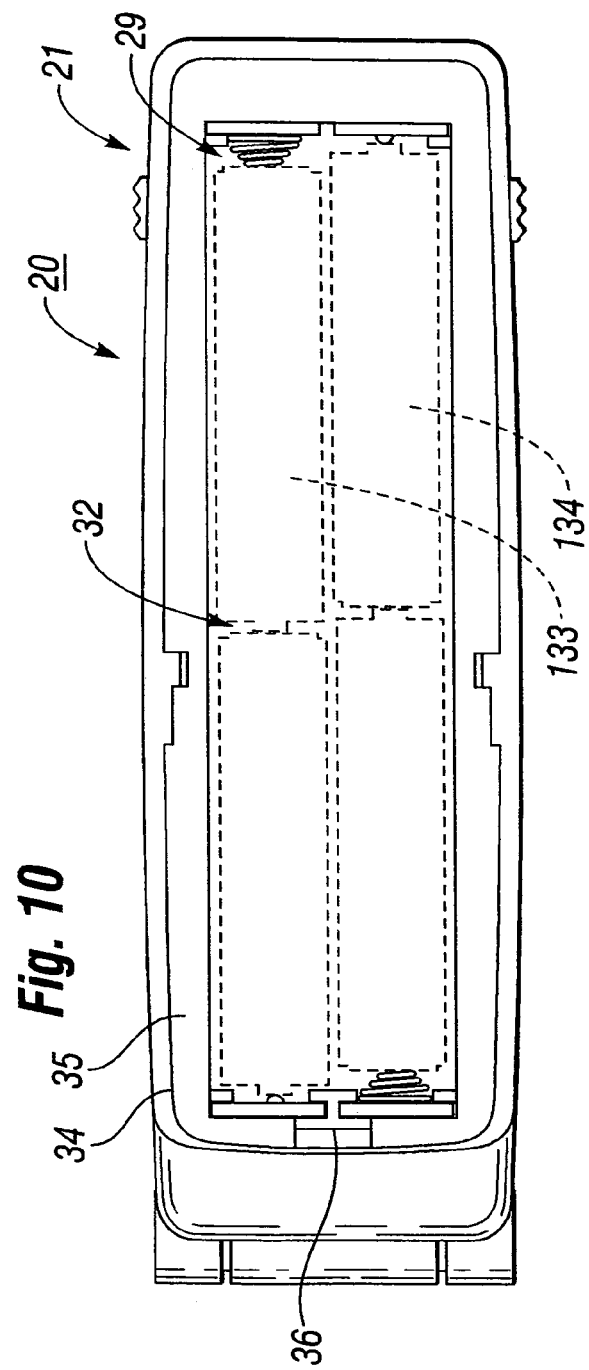
FIG. 10 is a view similar to that of FIG. 9, showing a battery compartment cover removed from a handle base housing portion of the apparatus.

As shown in FIGS. 9 and 10, handle base housing 21 has a hollow interior space 29 located between base wall 23 and cover wall 28. Hollow interior space 29 has an inner compartment 30 containing electronic circuitry 31 of apparatus 20, and an outer, battery compartment 32. The latter is accessible via a rectangularly shaped access door 33 which fits in a recess 34 provided in an aperture 35 through upper base wall 23, and releasably retained therein by a latch mechanism 36.

Figure 2:
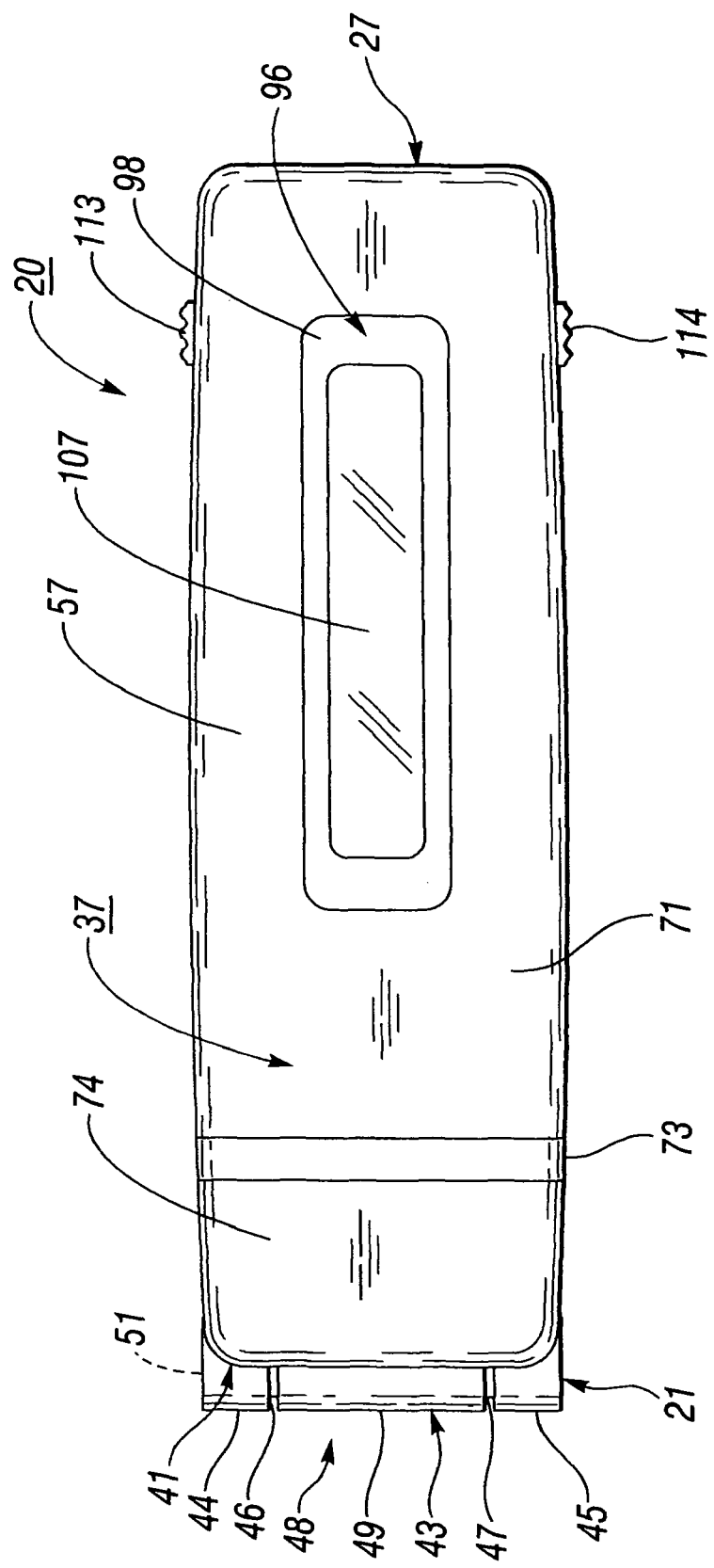
FIG. 2 is a lower plan view of the apparatus of FIG. 1.

Referring to FIGS. 1-3, it may be seen that disinfection apparatus 20 includes a lid 37 that has a flat lower wall surface 38 which in a closed configuration of the apparatus overlies and contacts the lower surface 39 of lower cover wall 28 of handle base housing 21. As shown in the figures, lid 37 has a longitudinally elongated rectangular plan-view shape similar in size to that of handle base housing 21, and is congruently aligned with the handle base housing when apparatus 20 is in a closed, inoperative position. As is also shown in the figures, lid 37 is thinner than base housing 21 and preferably has a convex, arcuately curved upper wall surface 40 which has a generally uniform transverse cross-sectional shape.

As may be seen best by referring to FIGS. 1-3, lid 37 is pivotably attached at a rear transverse edge 41 thereof to the lower edge 42 of front transverse flange wall 26 of handle base housing 21 by a tubular pin hinge joint 43. Hinge joint 43 includes a pair of laterally spaced apart, coaxially aligned left and right hinge support bosses 44, 45 which protrude forward from the front transverse edge wall 26 of handle 21. Handle hinge support bosses 44, 45 form between inner facing vertically disposed circular faces 46, 47 thereof a transversely disposed space 48.

Figure 14:
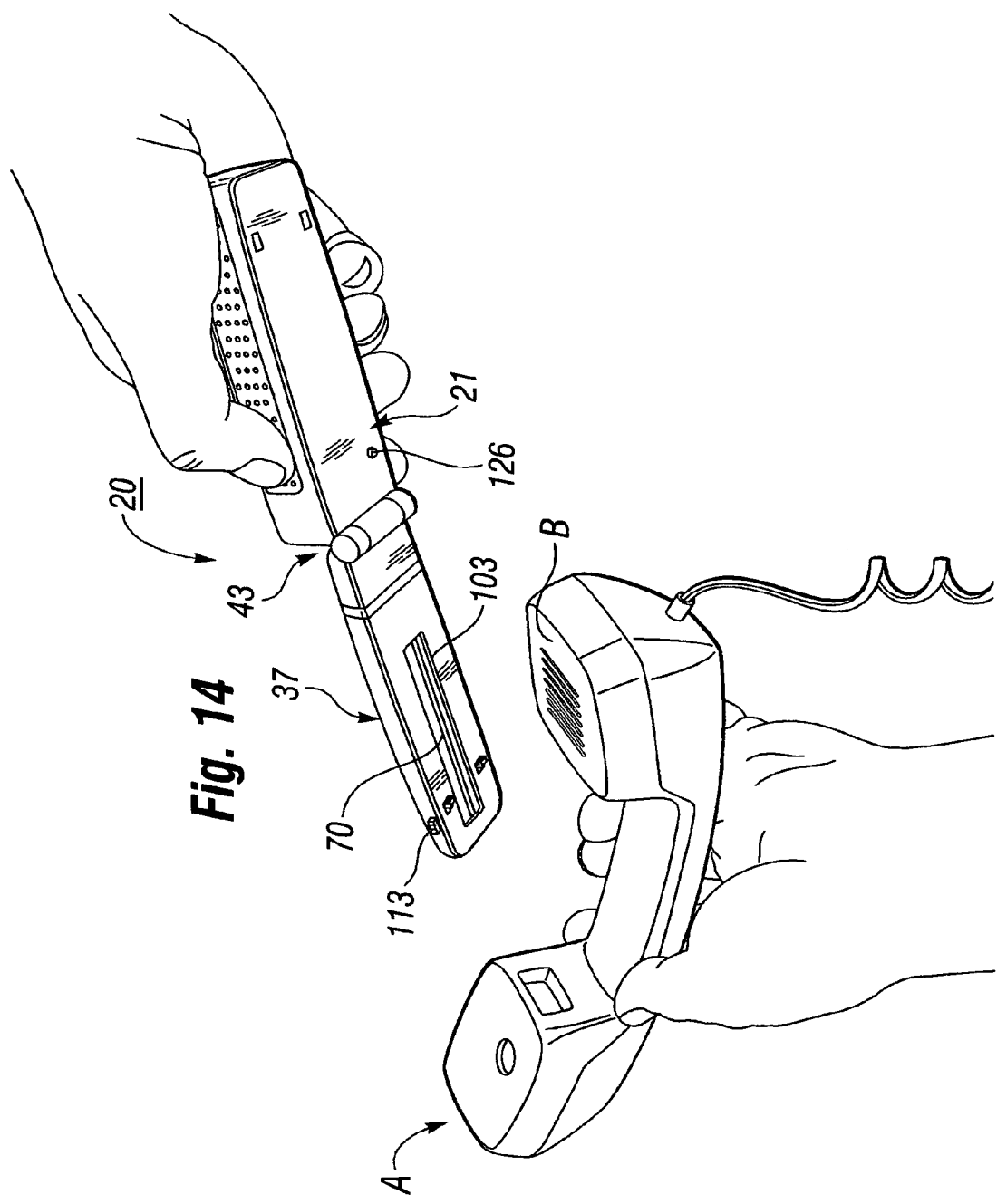
FIG. 14 is a lower perspective view of the apparatus of FIG. 6 showing the lid thereof pivoted into fully operational longitudinal alignment with the handle base housing thereof, and showing the apparatus being used to disinfect the microphone of a telephone handset.
Figure 15:
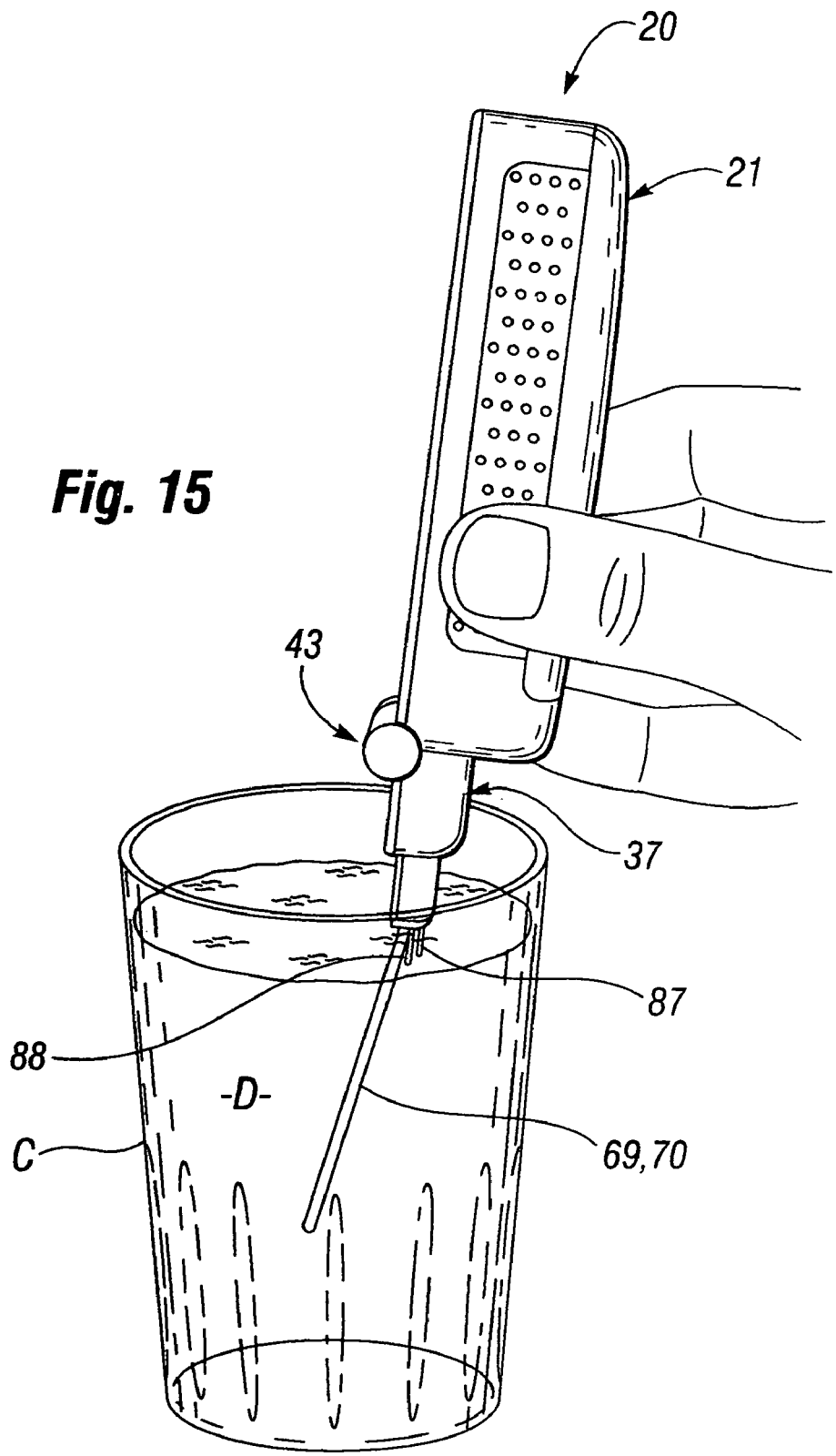
FIG. 15 is a perspective view showing the apparatus of FIG. 6 being used to disinfect water in a container.

Space 48 receives therein a relatively long, transversely disposed hinge cylinder 49 which protrudes rearwards from the rear transverse edge wall 41 of lid 37. Hinge joint 43 includes a hinge pin 51 which is disposed through coaxial aligned bores 52, 53 of left and right handle hinge support bosses 44, 45, and a bore 54 through hinge cylinder, 49 of lid 37. This construction enables lid 37 to be pivoted vertically about the longitudinal axis of hinge 43 from a closed, inoperative configuration as shown in FIGS. 1 and 2, to an open, operating position in which the lid is longitudinally aligned with the handle base housing 21, as shown in FIGS. 6, 14 and 15.

Referring to FIGS. 1-6, it may be seen that hinge cylinder 49 of lid 37 has protruding forward therefrom a symmetrically wider rectangular block-shaped portion 55A which has the same width as handle base housing 21. Rear hinge cylinder 49 and front block-shaped portion 55A together comprise a hinge block 55. As will be described in detail below, lid 37 includes a cover shell portion 57 which is releasably fastenable to lid hinge block 55.

As shown in FIG. 6, hinge block 55 has in lower plan view a rectangular T-shape which has a flat bottom surface. As shown in FIGS. 1-3, hinge block 55 has an upper convexly curved shell 74 which extends rearwardly over rear hinge cylinder 49. As shown in FIGS. 5A, 5B, 6 and 7, front block-shaped portion 55A of hinge block 55 has protruding from a transverse vertical front face thereof a lamp tube support bulkhead 56.

Lamp tube support bulkhead 56 has in front elevation view a semi-oval, or semi-elliptical shape, including a flat lower wall 76 and a semi-oval convex arcuately curved upper wall 77. Block-shaped portion 55A of hinge block 55 also has a semi-oval transverse cross-sectional shape, concentrically arranged with respect to lamp support bulkhead 56, but of larger perimeter, thus forming a semi-oval transversely disposed ring-shaped shoulder 78 at a transverse vertical junction plane between the lamp support bulkhead and front hinge block portion 55A.

As shown in FIGS. 3, 5B and 6, lamp support bulkhead 56 has a front vertically disposed transverse face 60. Hinge block 56 has protruding perpendicularly forward from front, vertical face 60 thereof a generally cylindrically-shaped lamp tube support boss 61. The lamp tube support boss 61 has extending rearwardly and inwardly into a front vertical transverse face 62 thereof a pair of left and right laterally spaced apart, tapered, resiliently deformable lamp terminal pin sockets 63, 64. The latter receive in a tight interference fit cylindrical lamp terminal pins 65, 66 which protrude rearwardly from left and right legs 67, 68 of the bulb 69 of a low-pressure ultraviolet mercury vapor discharge lamp 70. Terminal pins 65, 66 are disposed through rear end walls of the lamp 70 in hermetic vacuum-tight seals. Front portions of lamp terminal pins 65, 66 within the interior of lamp 70 comprise electrodes which are in contact with argon gas and mercury vapor within the lamp.

Bulb 69 of ultraviolet lamp 70 has the shape of a long, thin cylindrical body which has disposed through its length a hair-pin curve-shaped capillary bore having closely spaced, straight parallel legs 70L, 70R. Bulb 69 has an outer diameter of about 6 mm, ane a length of about 100 mm. Bulb 69 is made of a fused silica glass which has a high transmissibility for ultraviolet radiation in the range of 185 nm to 365 nm. Ultraviolet lamp 70 is a low-pressure gas discharge-type which contains therein about 5 milligrams of mercury, and argon gas. This mass of 5 milligrams of mercury contained in the internal volume of bulb 69 becomes partially vaporized and ionized when subjected to an applied voltage of 800 volts and a current of 2.5-3.5 milliamperes. The foregoing lamp characteristics and operating parameters result in ultraviolet radiation emission from ionized mercury vapor within the lamp which has a spectral emission range of about 185 nm to about 365 nm, and a peak emission at 253.7 nm, and a radiant power of about 2000 micro watts per square centimeter, at a distance of about 5 mm from lamp bulb 69.

Figure 8:
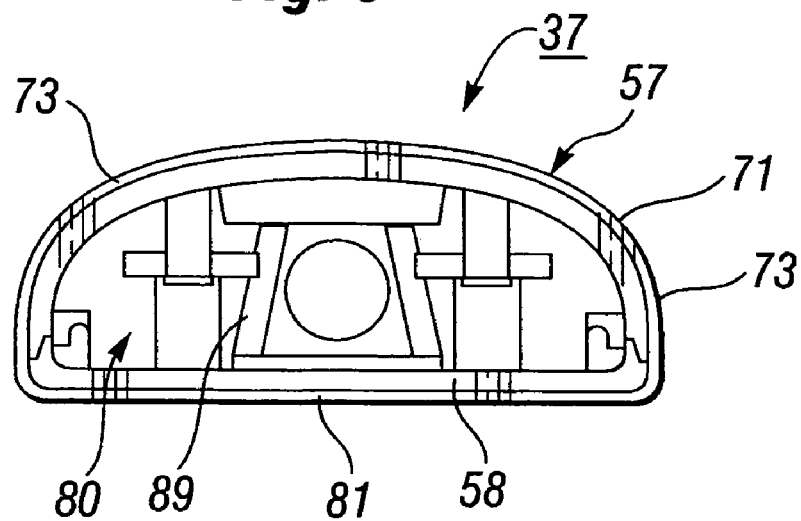
FIG. 8 is a rear elevation view of a lid portion of the apparatus of FIG. 6, taken in the direction of line 8-8.

As shown in FIGS. 1 and 8, cover shell 57 of lid 37 includes an upper longitudinally elongated convex upper wall portion 71. Upper wall portion 71 has the form of a thin, uniform thickness shell, which has an arcuately curved, convex generally uniform transverse cross-sectional outer shape, that protrudes upwardly from a rectangular base plate 58. Upper wall portion 71 of cover shell 57 has a longitudinally elongated rectangular plan view shape which is similar to the shape of base plate 58.

As shown in FIGS. 4-6, 5B and 8, upper wall portion 71 of cover shell 57 has a vertically disposed rear transverse end wall 73, that has the shape of a semi-oval annular ring. Rear transverse end wall 73 of lid cover 57 and upper surface 59 of base plates 58 circumscribe a semi-oval shaped longitudinally disposed bore 80 which is adapted to receive in a conformal, sliding fit front semi-oval shaped lamp support bulkhead 56. With cover 57 of lid 37 attached to lamp support bulkhead 56, the rear transverse end wall 73 of upper wall 71 conformally abuts the front transverse edge wall 75 of short rear cover shell 74 which overlies rear portion 55A of hinge block 55. With this arrangement, lower surface 81 of base plate 58 and lower surface 82 of hinge block 55 are in flush parallel alignment when lamp support bulkhead 56 is fully inserted into bore 80 of lid cover 57. Rear cover shell 74 also has a rear arcuately curved convex end wall 76.

FIGS. 3-6 and 12-13 illustrate features of apparatus 20 which facilitate slidable removal of cover shell 57 of lid 37 from handle base housing 21, to configure the apparatus for disinfecting water, and slidable re-attachment of the lid to the handle base housing to configure the apparatus for disinfecting object surfaces.

As shown in FIGS. 1-3 and 6, lid 37 of apparatus 20 includes a pair of left and right fastener pin bosses 83, 84 which are located on opposite sides of lamp tube support boss 61. Bosses 83, 84 which have a smaller diameter than lamp support boss 61, are symmetrically arranged with respect to the lamp support boss, and also protrude perpendicularly forward from front face 60 of lamp support bulkhead 56.

Bosses 83, 84 have protruding forward from front faces 85, 86 thereof left and right cylindrically-[shaped metal fastener pins 87, 88. The fastener pins are laterally aligned, and receivable in a resilient interference fit within an inverted C-shaped metal spring strip 89. As shown in FIG. 3, spring strip 89 is formed from a flat, longitudinally elongated rectangular metal strip which is disposed laterally over the upper surface 90 of lid base plate 58. Spring strip 89 has a pair of short laterally opposed outer end legs 91, 92 which are secured to the upper surface 90 of base plate 58, and an inverted C-shaped center section 94 which protrudes upwardly from the outer legs.

As may be seen best by referring to FIGS. 3-6, upper wall 71 of cover shell 57 of lid 37 has protruding downwards from a lower inner surface 95 thereof a longitudinally elongated, lamp reflector box 96. As shown in the figures, lamp reflector box 96 has in lower plan view a longitudinally elongated rectangular shape which is laterally centered with respect to lower rectangular wall surface 97 of lid 37.

As shown in FIGS. 1-6, reflector box 96 has a longitudinally elongated, rectangular plan view upper wall 98, left and right longitudinally elongated downwardly depending side walls 99, 100, and front and rear short vertically disposed transverse walls 101, 102, which protrude downwards from the upper wall. The side walls 99, 100 and transverse walls 101, 102 of reflector box 96 fit conformally within an elongated rectangularly-shaped aperture 103 through the thickness dimension of lid base plate 58, with the lower edges of the transverse and longitudinal side walls coplanar with lower surface 104 of the base plate.

As shown in FIGS. 3-6, front and rear transverse walls 101, 102 of reflector box 96, which preferably angle obliquely inwardly from the base plate towards the upper wall 98 of the reflector box, have through their thickness dimension front and rear circular clearance holes 105, 106, for insertably receiving ultraviolet lamp bulb 69. The inner wall surfaces of the reflector box walls which face lamp bulb 69 have formed thereon reflective metallic surfaces which are effective in reflecting ultraviolet radiation emitted from lamp bulb towards base plate aperture 103.

Optionally, at least a part 107 of upper wall 98 of reflector box 96 is made of an ultraviolet absorbing, visible-light transmissive material. This arrangement enables the small amount of visible light emitted by the ultraviolet lamp 70 to be viewed through the light transmissive portion 107 of the upper reflector wall, thereby confirming energization of the lamp to irradiate a surface beneath lid 37.

As shown in FIGS. 3, 4 and 5A-5C, lid 37 is provided with a pair of hooks laterally opposed, left and right latch hooks 108, 109, located a short distance rearward of front transverse edge 110 of lid base plate 58. Latch hooks 108, 109 are urged resiliently rearwards by springs 111, 112, respectively. The latch hooks 108, 109 have laterally outwardly protruding grooved finger buttons 113, 114 which protrude laterally outwardly through apertures 115, 116 provided in sides 117, 118 of cover shell 57.

As shown in FIG. 5C, latch hooks 108, 109 have at lower ends thereof rearwardly and upwardly angled tangs 119, 120. When latch hooks 108, 109 are moved forwards by finger pressure on both finger buttons 113, 114, tangs 119, 120 at the lower ends of the hooks are vertically alignable with and insertable into individual ones of a pair of laterally opposed, rectangular left and right slots 121, 122 through the thickness dimension of lower cover wall 28 of handle base housing 21. Releasing finger pressure on the latch buttons enables the latch hook tangs to be urged resiliently rearward by the latch springs, causing the upper surfaces of the tangs to lodge against the inner surface 123 of the handle base housing cover wall. This arrangement maintains the lid 37 in a closed, inoperative position until the finger buttons are simultaneously moved by an adult hand.

Figure 11:
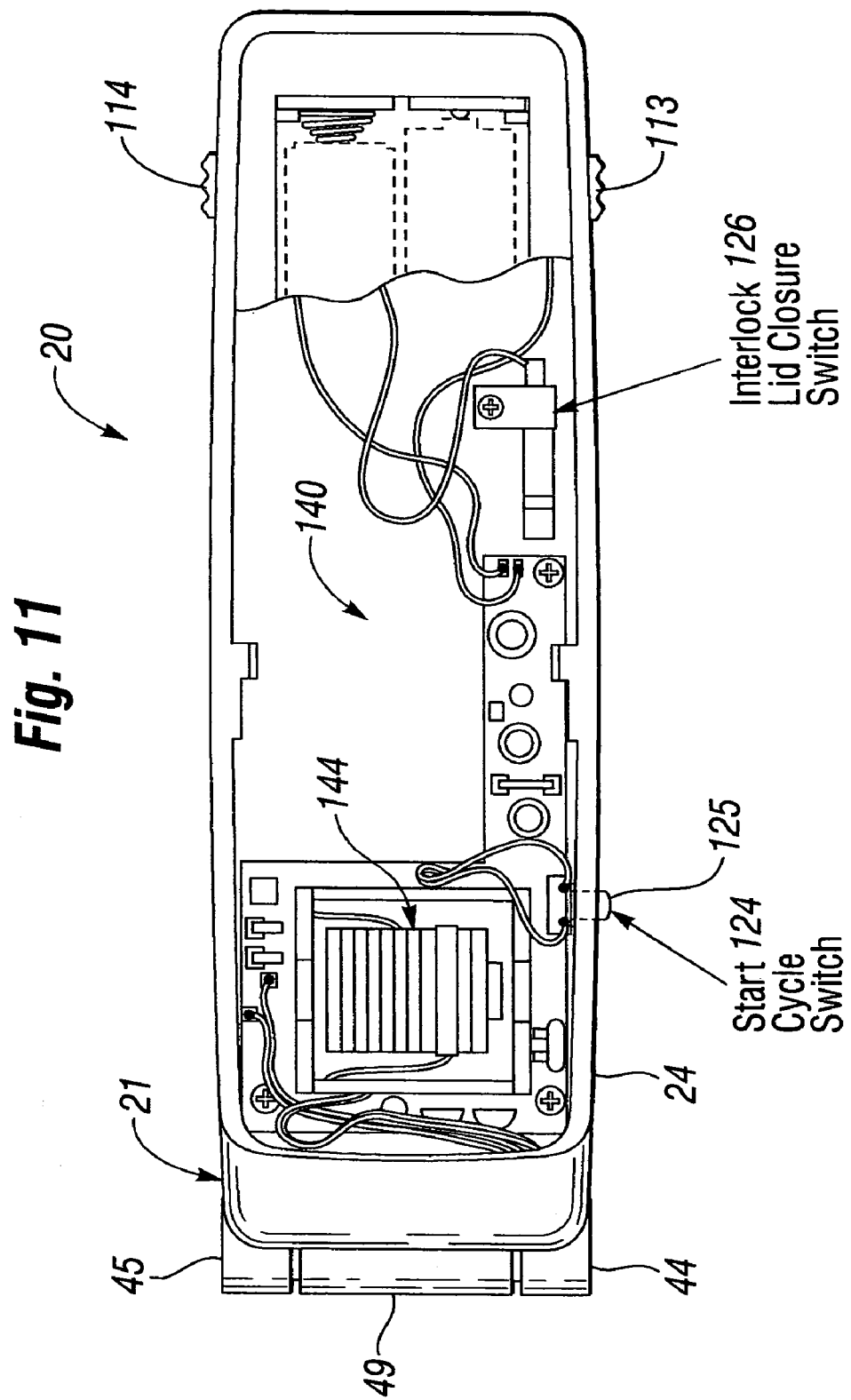
FIG. 11 is a fragmentary, partly broken-away upper view of a handle base housing portion of the apparatus of FIG. 8, showing electronic components thereof.
Figure 12:
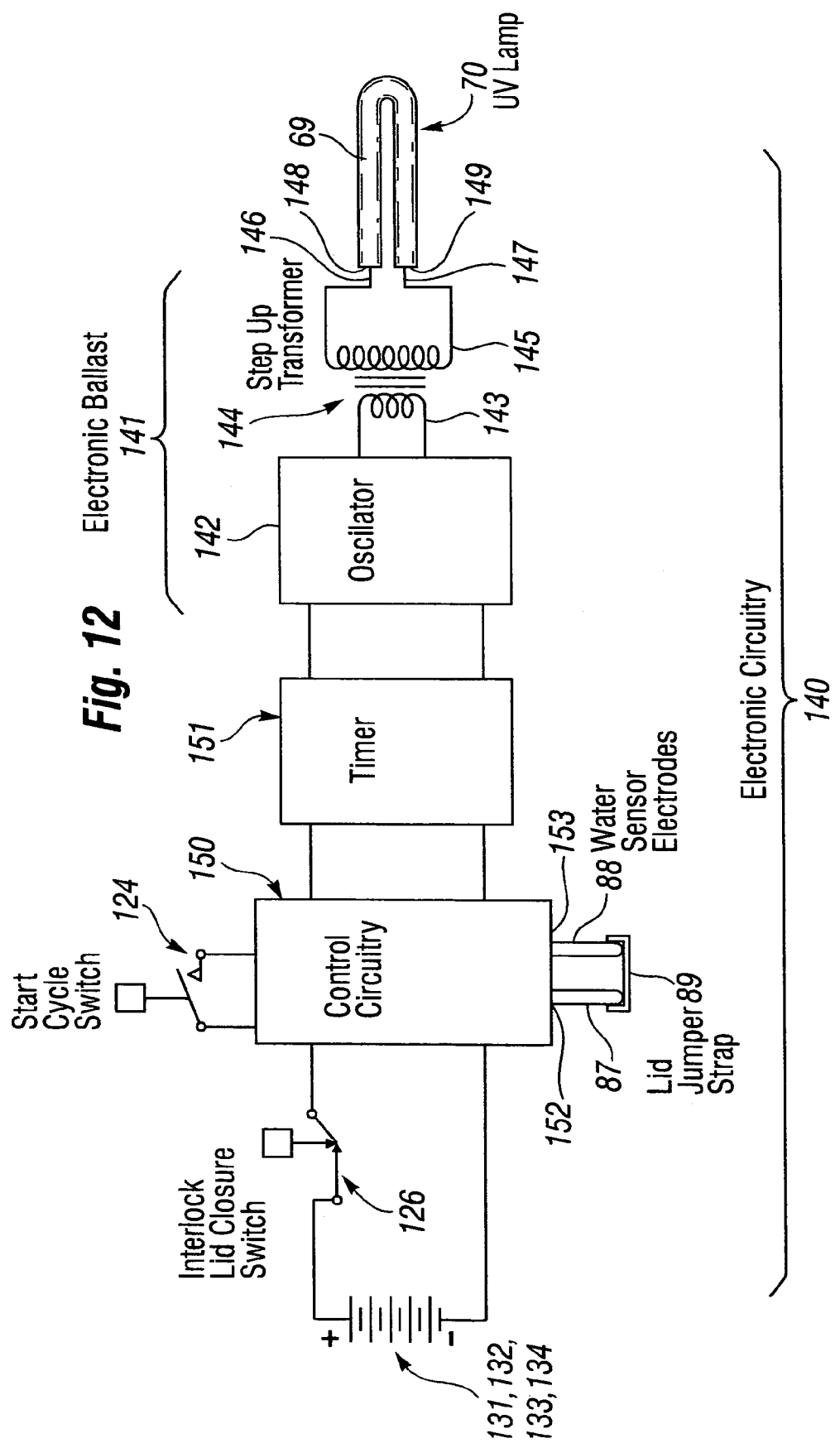
FIG. 12 is a block diagram of the apparatus of FIG. 1.

As shown in FIGS. 11 and 12, apparatus 20 includes a normally open push button switch 124 which has a finger button 125 that protrudes through left side wall 24 of handle base housing 21. Also, as shown in FIGS. 4, 11 and 12, apparatus 20 has a interlock switch 126 which has a button 127 that protrudes downwardly through a circular hole 128 through lower cover wall 28 of handle base housing. Switch 126 is a normally closed switch, which interrupts electrical continuity through the switch contacts when lower surface 128 forces button 127 upwardly when contacted by lower surface 128 of lid base plate 58, when the lid is closed. Switches 124 and 126 are electrically interconnected with control circuitry 140 of apparatus 20, which will now be described.

FIG. 12 is an electrical block diagram of disinfection apparatus 20. As shown in FIGS. 11-12, apparatus 20 includes electronic circuitry 140 for converting low voltage electrical power supplied by batteries 131, 132, 133, 134 located in battery compartment 32 (see FIG. 8) into high-voltage low current electrical power for energizing ultraviolet discharge lamp 70.

As shown in FIG. 12, electronic circuitry 140 of apparatus 20 includes a DC-to-AC inverter 141, commonly referred to as an electronic ballast. Electronic ballast 141 includes a transistor oscillator 142 which converts direct current power supplied by batteries 132-134 to alternating current which is conducted through the primary coil 143 of a step-up transformer 144. Step-up transformer 144 has a secondary coil 145 which has a turns ratio relative to the primary coil of about 140:1. Thus, for a battery supply voltage of about 6 volts, the voltage of output terminals 146, 147 of secondary coil is about 840 volts. That voltage, when applied to terminals 148, 149 of ultraviolet lamp 70, is sufficient to ionize argon gas with the envelope of the lamp bulb, which in turn causes mercury within the envelope to vaporize. Electrical current flowing through the mercury vapor produces ultraviolet radiation emissions. Although the operating frequency of oscillator 142 is a matter of design choice, a suitable operating frequency is about 30-40 KHz.

As shown in FIG. 12, electronic circuitry 140 includes control circuitry 150 and a timer circuit 151 for controlling the duration of d.c. battery power input to electronic ballast 141, and thus controlling the duration of UV radiation emitted by lamp 70.

Referring still to FIG. 12, it may be seen that d.c. electrical current from batteries 131-134 is conducted to control circuitry 150 through normally closed lid closure interlock switch 126. Switch 126 is closed to enable current flow when lid 37 is pivoted away from handle base housing 21, and opened to interrupt current flow to control circuitry 150 when the lid is closed and latched to the handle base housing.

As shown in FIG. 12, control circuitry 150 has input sensor terminals 152, 153 which are electrically conductively connected to fastener pin/sensor probes 87, 88, respectively. Control circuitry 150 includes transistor sensor circuitry which supplies a low sampling voltage of about 6 volts to terminals 152, 153 and fastener pin/sensor probes 87,88. The sensor circuitry includes a transistor switch which is turned from an OFF state to an ON state when a current as small as about 0.3 micro amperes flows between sensor pins 87 and 88 as a result of being immersed in water having a conductivity as low as about 18 megohm-cm. Thus, when lid 37 is removed from apparatus 20, and lamp 77 and sensor probes 87,88 immersed in water, control circuitry 150 is switched to an operative state. Similarly, when lid 37 is reattached to handle base housing 21, electrically conductive contact between sensor probes 87,88 established by lid jumper strap 89 enables operation of control circuitry 150.

When control circuitry 150 is enabled as described above, momentarily depressing start cycle push-button switch 124 latches the control circuitry into an active conductive state in which battery current is applied to oscillator 142 of electronic ballast 141, for a period determined by timer circuit 151. That time period is determined by the intensity of UV radiation emitted by lamp 70, and the amount of energy required to kill organisms at a particular distance from the lamp 70. In an example embodiment of apparatus 20, timer 151 was set to deliver UV radiation from lamp 70 for a duration of about 12 seconds.

Figure 13:
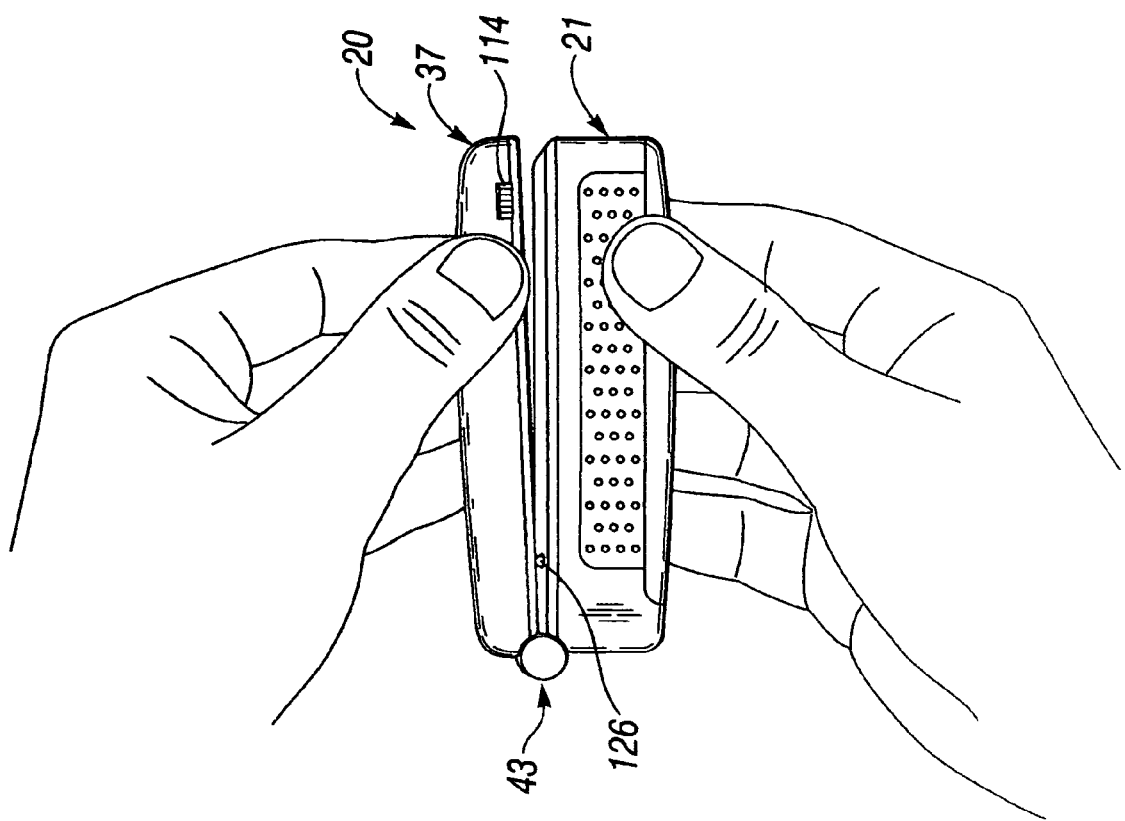
FIG. 13 is a perspective right-hand view of the apparatus of FIG. 1, showing how a lid portion thereof is pivoted upwards from a handle base housing portion thereof, to reconfigure the unit from an inoperative configuration to an operative configuration.

FIGS. 13 and 14 illustrate how disinfecting apparatus 20 may be used to disinfect an object surface, such as the microphone of a telephone handset.

Referring first to FIG. 13, apparatus 20 is re-configured from a first, closed inoperative storage and transport configuration to an open, operative configuration by pushing forward on left and right latch hook finger buttons 113, 114, on opposite sides of lid 37. This may be conveniently done by using the thumb and forefinger of a person's hand. Simultaneously pushing latch buttons 113, 113, causes latch hooks 108, 109 attached to the hooks to disengage from slots 121, 122 through lower cover wall 28 of base housing 21. Releasing hooks 108, 109 from slots 121, 122 enables lid 37 to be pivoted upwardly from base housing 21 to an orientation in which the lid is longitudinally aligned with the base housing, and the apparatus inverted as shown in FIG. 14.

Pivoting lid 37 upwards from lower cover wall 28 enables push button of interlock switch 126 to extend outwardly through upper cover wall 128 of handle base housing 21 in response to pressure of a spring within the mechanism of the interlock switch 126. As shown in FIG. 12, closure of contacts of a switch 126 completes a path for current from batteries 121-124 to control circuitry 150 of electronic circuitry 140. With power applied to control circuitry 150, momentarily depressing push button 125 of start cycle switch 124 causes timer circuit 151 to enable battery current to be supplied to electronic ballast 141 for a predetermined time periods, e.g., 12 seconds. Lamp 70 is thus energized for about 12 seconds, and may be used to disinfect microphone B of a telephone handset A by positioning aperture 103 through lid 57 in close proximity to the microphone, and manipulating handle base housing 21 to cause ultraviolet radiation emitted through aperture 103 to irradiate the surface of the microphone in an overlapping, scanning motion. FIGS. 4-6 and 15 illustrate how apparatus 20 may be used to disinfect drinking water contained in a drinking glass or other small drinking vessel.

As shown in FIG. 13, lid 37 of apparatus 20 is unlatched from handle base housing 21, and pivoted into longitudinal alignment with the base housing, in the manner described above. Then, as shown in FIG. 5, cover shell portion 57 of lid 37 of apparatus 20 is grasped and pulled away from lamp support bulkhead 56 protruding from hinge block 55 attached to handle base housing 21, until the lid cover is completely removed, as shown in FIG. 6.

With apparatus 20 configured for disinfecting water by removing lid cover 57 from handle base housing 21 as described above, lamp bulb 69 is inserted into water D in a container C such as a drinking glass, as shown in FIG. 15. The lamp bulb 69 is immersed sufficiently deeply within water D until fastener pin/sensor probes 87, 88 are also immersed in the water. Referring to FIG. 12, the electrical conductivity of the water enables control circuitry 150 to respond to actuation of push button start cycle switch 124, thus energizing lamp 70 for a predetermined time interval, as described above. Lamp bulb 69 is then moved in a stirring motion in water during the time that ultraviolet lamp 70 is energized thus emitting ultraviolet radiation into the water and disinfecting the water.

As described above, a primary function of cover 57 of apparatus 20 is to prevent ultraviolet radiation emitted from lamp 70 from being directed towards the eyes of a user of the apparatus, because of possible undesirable effects on human vision.

Cover 57 also provides a safety interlock feature, which prevents energization of lamp 70 when cover 57 is removed, unless the lamp and consequently sensor probes 87, 88 are fully immersed in a liquid, such as water in a container. Since water is an efficient absorber of shortwave ultraviolet radiation in a wavelength range which could have adverse effects on the eyes, such radiation is prevented from being transmitted from a vessel such as a drinking glass in which lamp 70 is immersed.

The foregoing functions of cover 57 could optionally be performed by a simpler construction, in which the cover consisted simply of an elongated thin plate which overlay the upper surface of the lamp 70, and had protruding from the lower surface of the plate a receptacle such as a spring metal strap for resiliently and electrically conductively receiving sensor probes 87,88. In such a variation of the present invention, the metal plate would preferably have a concave, e.g., parabolic, reflective lower surface adjacent to the lamp 70.

Figure 16:
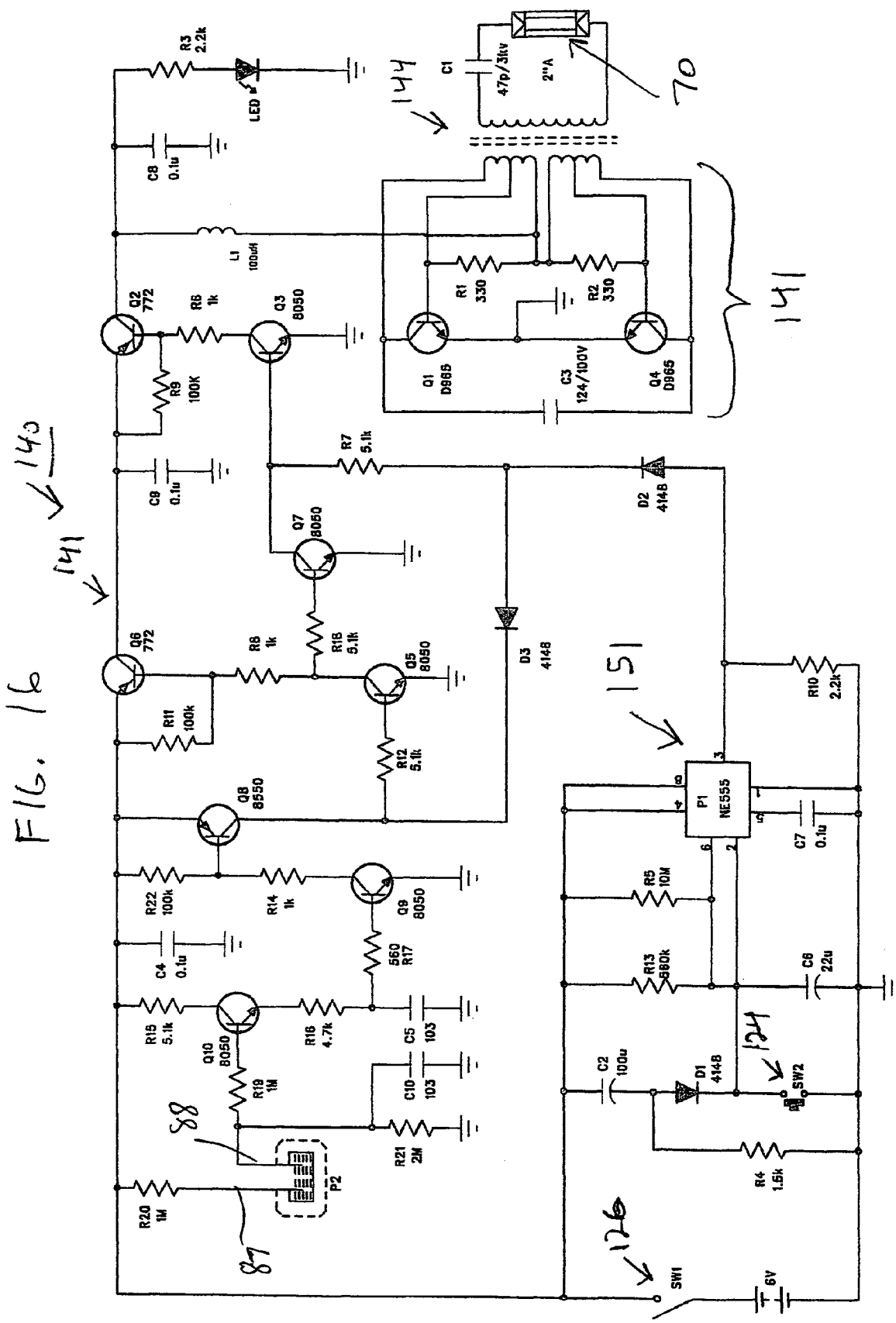
FIG. 16 is an electrical schematic diagram of the apparatus shown in block diagram form in FIG. 12.

FIG. 16 is an electrical schematic diagram of apparatus 20, shown in block diagram form in FIG. 12. As shown in FIG. 16, apparatus 20 optionally may be provided with an LED indicator lamp 307 mounted in lid 37, in which case window 107 may be eliminated.

What is claimed is:

1. An apparatus for alternatively disinfecting an object surface and a liquid comprising;
 a. a hollow handle base housing,
 b. an electrical power source contained within a hollow interior space of said handle base housing for supplying electrical power to an electrically energizable radiation source,
 c. a radiation source support structure connected to said handle base housing for supporting a radiation source,
 d. an electrically energizable radiation source effective in killing microorganisms mounted to said radiation source support structure,
 e. electrical conductors electrically conductively connected between said power source and said radiation source, and
 f. a cover releasably attached to said radiation source support structure, said cover having an upper wall effective in blocking radiation emitted upwardly from said radiation source and having an aperture through a lower side of said cover which enables radiation from said radiation source to pass through and irradiate an object surface, said cover being alternatively removable to enable said radiation source to be immersed in and irradiate a liquid, and replaceable to irradiate an object surface.

2. The apparatus of claim 1 further including a sensor mechanism electrically connected to said power source, said sensor mechanism inhibiting energization of said radiation source with said cover removed unless said radiation source is immersed in a liquid to irradiate the liquid.

3. The apparatus of claim 2 wherein said sensor mechanism is further defined as including in combination a pair of electrically conductive sensor probes located proximate said radiation source, and an electronic switch electrically connected to said sensor probes, said electronic switch interrupting supply of electrical power to said radiation source unless an electrically conductive path having a predetermined minimum electrical conductivity exists between said sensor probes.

4. The apparatus of claim 3 further including an electrically conductive jumper member located within said radiation source cover, said jumper member forming an electrically conductive path between said sensor probes when said cover is attached to said radiation source support structure.

5. The apparatus of claim 1 wherein said radiation source is further defined as an electrical lamp which emits ultraviolet radiation.

6. The apparatus of claim 5 wherein said lamp is further defined as being a mercury vapor discharge lamp.

7. The apparatus of claim 6 wherein said mercury vapor discharge lamp is further defined as including an elongated ultraviolet-transmissive body having therein a sealed bore having a pair of first and second parallel bore legs joined near an outer longitudinal end of the body by a U-shaped curved bore.

8. The apparatus of claim 7 wherein said parallel legs and said U-shaped curved bore comprise in combination a unitary, hair-pin curve-shaped bore.

9. The apparatus of claim 8 wherein said parallel legs of said bore are terminated in a sealed rear transverse end wall.

10. The apparatus of claim 9 wherein said rear transverse end wall has disposed therethrough a pair of first and second electrodes which communicate with separate ones of said first and second legs of said bore.

11. The apparatus of claim 10 wherein said lamp body is made of silica.

12. The apparatus of claim 10 wherein said lamp body bore contains argon gas and elemental mercury.

13. An apparatus for alternatively disinfecting an object surface and a liquid comprising;
 a. a hollow handle base housing graspable in a human hand,
 b. an electrical power source contained within a hollow interior space of said handle base housing for supplying electrical power to an ultraviolet lamp,
 c. an ultraviolet lamp support structure for supporting an ultraviolet lamp,
 d. an ultraviolet lamp mounted to said ultraviolet lamp support structure,
 e. a hinge joint pivotably joining said ultraviolet lamp support structure to said handle base housing, said hinge joint enabling said ultraviolet lamp support structure and ultraviolet lamp to be pivoted from a first compact storage and transport orientation in which said lamp is positioned closely to said hollow handle base housing, to a second, use orientation in which said lamp protrudes outwardly from said handle base housing, f. electric lamp power conductors electrically conductively connected between said power source and said ultraviolet lamp, and g. a lamp cover releasably attached to said ultraviolet lamp support structure, said cover having an upper wall overlying said ultraviolet lamp to thus overly said ultraviolet lamp with said hinge support structure in said first orientation relative to said handle base housing, said cover having in a lower side adjacent to a lower side of said ultraviolet lamp an aperture which enables ultraviolet radiation emitted by said ultraviolet lamp to irradiate an object surface below which said apparatus may be positioned, said cover being alternatively releasably removable from said ultraviolet lamp support structure to enable said ultraviolet lamp to be immersed in and irradiate a liquid, and replaceable to irradiate an object surface.

14. The apparatus of claim 13 further including a sensor mechanism electrically connected to said power source, said sensor mechanism inhibiting energization of said ultraviolet lamp with said cover removed unless said ultraviolet lamp is immersed in a liquid to irradiate the liquid.

15. The apparatus of claim 14 wherein said sensor mechanism is further defined as including in combination a pair of electrically conductive sensor probes located proximate said ultraviolet lamp, and an electronic switch electrically connected to said sensor probes, said electronic switch being responsive to electrical conductance between said sensor probes to inhibit application of electrical power to said ultraviolet lamp unless an electrically conductive path having a predetermined minimum electrical conductivity exists between said sensor probes.

16. The apparatus of claim 15 further including an electrically conductive jumper member located within said lamp cover, said jumper member forming an electrically conductive path between said sensor probes when said lamp cover is attached to said ultraviolet lamp support structure.

17. The apparatus of claim 16 wherein said ultraviolet lamp is further defined as having a base having electrical terminal pins which protrude rearwardly to make electrically conductive contact with said lamp power conductors within said lamp support structure, and an elongated body which protrudes forward from said base.

18. The apparatus of claim 17 wherein said ultraviolet lamp is further defined as being a mercury vapor discharge lamp.

19. The apparatus of claim 18 wherein said mercury vapor discharge lamp is further defined as including an elongated ultraviolet-transmissive body having therein a sealed bore having a pair of first and second parallel bore legs joined near an outer longitudinal end of the body by a U-shaped curved bore.

20. The apparatus of claim 19 wherein said parallel legs and said U-shaped curved bore comprise in combination a unitary, hair-pin curve-shaped bore.

21. The apparatus of claim 20 wherein said parallel legs of said bore are terminated in a sealed rear transverse end wall.

22. The apparatus of claim 21 wherein said rear transverse end wall has disposed therethrough a pair of first and second electrodes which communicate with separate ones of said first and second legs of said bore.

23. The apparatus of claim 22 wherein said lamp body is made of silica.

24. The apparatus of claim 22 wherein said lamp body bore contains argon gas and elemental mercury.

25. An apparatus for alternatively disinfecting an object surface and a liquid comprising;

a. a hollow handle base housing graspable in a human hand, b. an electrical power source contained within a hollow interior space of said handle base housing for supplying electrical power to an ultraviolet lamp, c. a lid including a lamp support bulkhead, an ultraviolet lamp mounted to said lamp support bulkhead, and a tubular cover shell releasably attachable to said lamp support bulkhead, said cover shell having an upper wall which is opaque to ultraviolet radiation and a lower wall which has therein an aperture which is transmissible to ultraviolet radiation, said cover being alternatively releasably removable from said lamp support bulkhead, to enable said ultraviolet lamp to be immersed in and irradiate a liquid, and replaceable to irradiate an object surface, d. a hinge joint which pivotably joins said lamp support bulkhead of said lid to said handle base housing, said hinge joint enabling said lid to be pivoted from a first, compact storage and transport orientation in which said lower wall of said lid cover shell overlies said handle base housing, and said upper wall of said lid cover shell overlies said ultraviolet lamp, to a second, use orientation in which said lid is positionable above an object surface to thereby locate said aperture adjacent to said object surface, e. electrical conductors connected between said electronic power source and said ultraviolet lamp.

26. The apparatus of claim 25 further including a sensor mechanism electrically connected to said power source, said sensor mechanism inhibiting energization of said ultraviolet lamp when said cover shell is removed unless said lamp is immersed in a liquid.

27. The apparatus of claim 26 wherein said sensor mechanism is further defined as including in combination first and second electrically conductive sensor probes located proximate said ultraviolet lamp, and an electronic switch electrically conductively connected to said sensor probes, said electronic switch being responsive to existence of an electrically conductive path of a predetermined minimum conductivity between said sensor probes to enable power to be provided to said ultraviolet lamp by said power supply, and disable application of power if said conductivity is below said predetermined value.

28. The apparatus of claim 27 wherein said sensor probes are further defined as being first and second electrically conductive members which protrude from said lamp support bulkhead.

29. The apparatus of claim 28 wherein said lid cover shell is further defined as having an electrically conductive member which conductively contacts said sensor probes when said lamp support bulkhead is fully engaged with said cover shell.

30. The apparatus of claim 29 further including an interlock switch which disables operation of said power supply when said lid is closed.

31. The apparatus of claim 30 wherein said power supply is further defined as including in combination a timer circuit and a start switch responsive to actuation by a human hand to thereby energize said ultraviolet lamp for a predetermined time period.

\* \* \* \* \*